US00PP29538P2

(12) United States Plant Patent
Smith

(10) Patent No.: US PP29,538 P2
(45) Date of Patent: Jul. 24, 2018

(54) ***CHRYSANTHEMUM* PLANT NAMED 'CIFZ0044'**

(50) Latin Name: *Chrysanthemum x morifolium*
Varietal Denomination: CIFZ0044

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,566

(22) Filed: Jan. 30, 2017

(51) Int. Cl.
*A01H 5/02* (2018.01)

(52) U.S. Cl.
USPC ..... Plt./292

(58) Field of Classification Search
USPC ..... Plt./292
See application file for complete search history.

*Primary Examiner* — Annette H Para
(74) *Attorney, Agent, or Firm* — Dale Skalla

(57) ABSTRACT

A new garden type *Chrysanthemum* plant named 'CIFZ0044' particularly distinguished by the medium-small (1.75 inch) red decorative flower, a medium sized plant with round mound habit and a natural season response in the end of September.

1 Drawing Sheet

Figure 1:
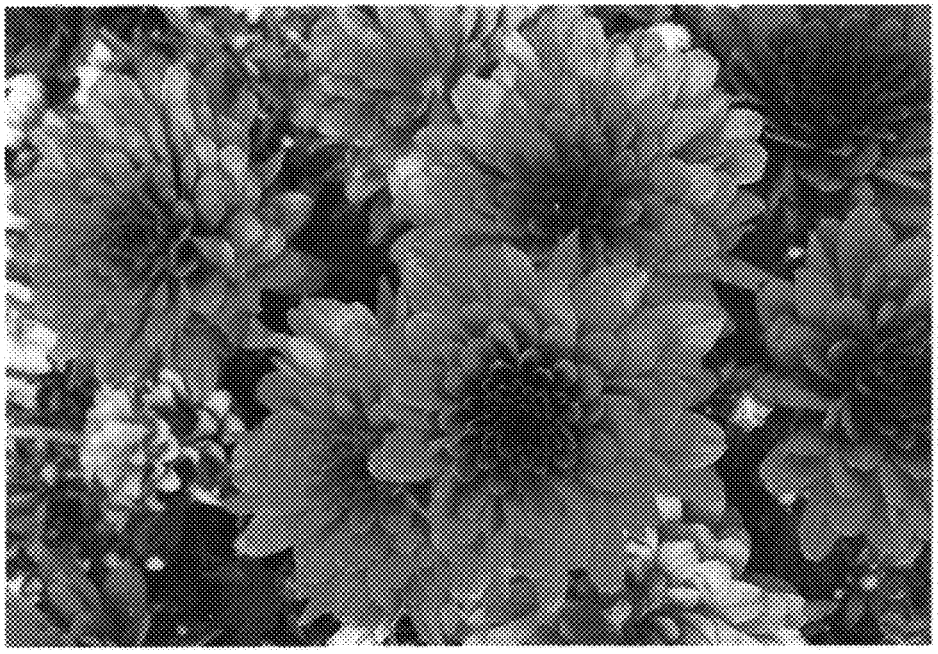

Latin name of the genus and species of the plant claimed: *Chrysanthemum x morifolium.*

Varietal denomination: 'CIFZ0044'.

BACKGROUND OF THE NEW PLANT

The present invention comprises a new *Chrysanthemum*, botanically known as *Chrysanthemum x morifolium*, and hereinafter referred to by the variety name 'CIFZ0044'.

'CIFZ0044' is a product of a planned breeding program. The new cultivar has medium-small (1.75 inch) red decorative flower, a medium sized plant with round mound habit and a natural season response in the end of September.

'CIFZ0044' originated from a cross made in December 2010 in Amatitlan, Guatemala.

The female parent was 'Zanmufive', U.S. Pat. No. 19,791, commercially known as 'Five Alarm Red'.

TABLE 1

| When compared to the female parent, 'CIFZ0044' has |
|---|
| (1) Similar flower type and color but smaller in size than 'Five Alarm Red' |
| (2) Natural season response is two weeks slower and blackcloth response 7 to 10 days slower than 'Five Alarm Red' |
| (3) Simlar plant size with less plant width and rounder plant habit than 'Five Alarm Red' |
| (4) More uniform flowering than 'Five Alarm Red' |

The male parent was an unnamed seedling from own breeding '07-M168'.

TABLE 2

| When compared to the male parent, 'CIFZ0044' has: |
|---|
| (1) Similar flower color with smaller flower size and less disc florets than the male parent |

TABLE 2-continued

| When compared to the male parent, 'CIFZ0044' has: |
|---|
| (2) Blackcloth response is a half a week slower and natural season response is a half a week faster than the male parent |
| (3) Similar plant habit and plant size as the male parent |

The resultant seed was sown in June 2011 in Gilroy, Calif.

The first act of asexual reproduction of 'CIFZ0044' was accomplished when vegetative cuttings were propagated from the initial selection, this initial selection took place Nov. 1, 2011 in Monroeville, N.J.

BRIEF SUMMARY OF INVENTION

Horticultural examination of plants grown from cuttings of the plant initiated in January 2012 in Monroeville, N.J., and continuing thereafter, has demonstrated that the combination of characteristics as herein disclosed for 'CIFZ0044' are firmly fixed and are retained through successive generations of asexual reproduction.

'CIFZ0044' has not been observed under all possible environmental conditions. The phenotype may vary significantly with variations in environment such as temperature, light intensity and day length.

'CIFZ0044' has not been made publicly available prior to the effective filing date of this application, notwithstanding any disclosure that may have been made less than one year prior to the effective filing date of this application by the inventor or another who obtained 'CIFZ0044' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0044' with colors being as true as possible with an illustration of this type. The photographic drawings show in FIG. 1 a close view of flower of the new variety and in FIG. 2 a flowering plant from an outdoor trial.

Figure 2:
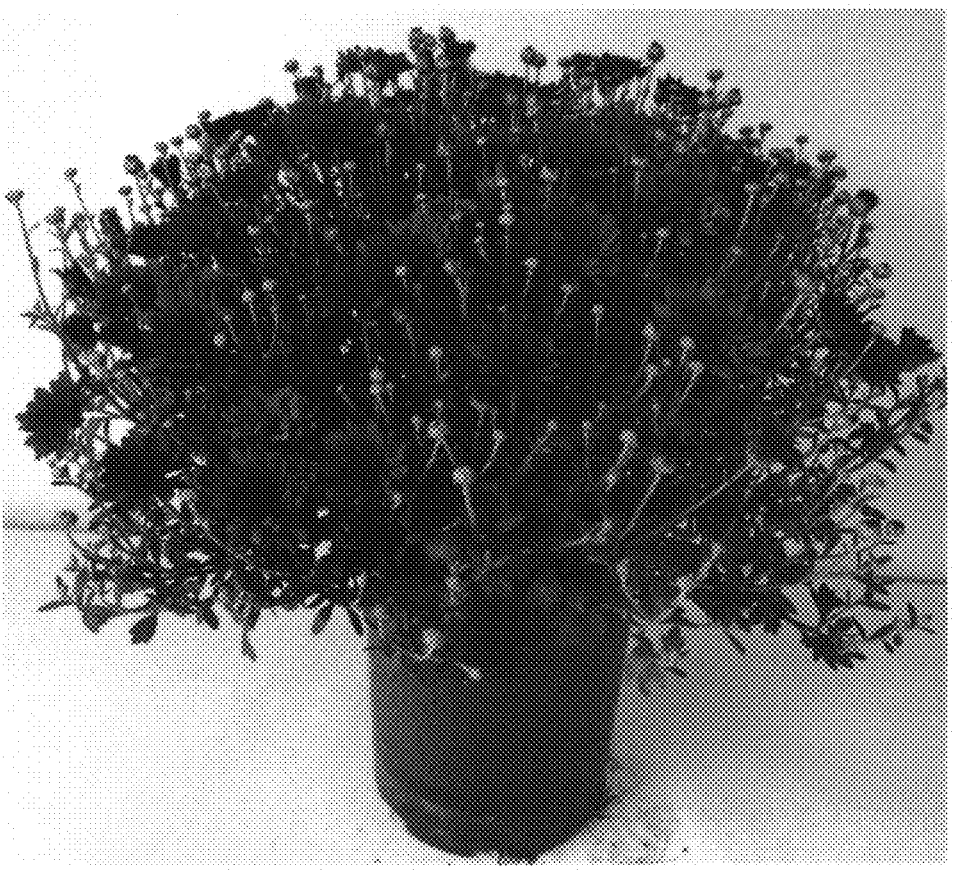

The aforementioned photographs: FIG. 1, as well as FIG. 2, were taken in August 2016 both showing a plant from the same natural outdoor trial in Gilroy, Calif. These plants were about 11 weeks of age. One rooted cutting per pot had been planted in a one gallon pot, not pinched in week 22. Plants started flowering in August.

DETAILED BOTANICAL DESCRIPTION

The measurements were taken in Gilroy, Calif. in August 2016 on the plants from the aforementioned trial.

Color references are made to The Royal Horticultural Society Colour Chart (R.H.S.) 2001.

TABLE 3

DIFFERENCES BETWEEN THE NEW VARIETY 'CIFZ0044' AND TWO MOST SIMILAR VARIETIES:

| | 'CIFZ0044' | 'Yobrandi', U.S. Plant Pat. No. 16,134 |
|---|---|---|
| Flowering response (blackcloth): | Half a week slower | Half a week faster |
| Flowering response (natural): | Similar | Similar |
| Flower color: | Bit lighter red color | Bit darker red color |
| Flower shape: | Similar | Similar |
| Flower size: | Smaller | Bigger |
| Plant habit or size: | Taller plant, round plant habit | Shorter plant. Semi-spreading habit |

TABLE 4

| | 'CIFZ0044' | 'Zanmuradiant', U.S. Plant Pat. No.25,013 |
|---|---|---|
| Flowering response (blackcloth): | Half a week faster | Half a week slower |
| Flowering response (natural): | Two days faster | Two days slower |
| Flowering uniformity: | More uniform | Less uniform |
| Flower color: | Similar | Similar |
| Flower size: | Smaller | Bigger |

Plant:

*Form, growth and habit.*—Herbaceous garden-type, stems upright and outwardly spreading, freely branching, strong and moderately vigorous growth habit.

*Plant height (above soil).*—19-21 cm.

*Plant height (inflorescence included).*—23-25 cm.

*Plant width.*—37-39 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137B.

*Immature leaf, color lower surface.*—RHS 137D.

*Mature leaf, color, upper surface.*—RHS 137A.

*Mature leaf, color lower surface.*—RHS 137C.

*Length.*—3.0-3.5 cm.

*Width.*—2.5-2.8 cm.

*Shape.*—Ovate.

*Base shape.*—Attenuate.

*Apex shape.*—Acute.

*Margin.*—3 main lobes, irregularly serrulated.

*Texture, upper surface.*—Bifid hairs.

*Texture, lower surface.*—Bifid hairs.

*Color of veins, upper surface.*—RHS 138A.

*Color of veins, lower surface.*—RHS 138A.

*Pattern of veining.*—Palmate.

*Petiole color.*—RHS 137B.

*Petiole length.*—1.1-1.3 cm.

*Diameter.*—0.1-0.2 cm.

*Texture.*—Covered with bifid hairs.

Stem:

*Quantity of main branches per plant.*—11-13.

*Color of stem.*—RHS 146B.

*Length of stem.*—9-12 cm.

*Diameter.*—0.4-0.6 cm.

*Length of internodes.*—1.5-2 cm.

*Texture.*—Bifid hairs.

*Color of peduncle.*—RHS 137C.

*Length of peduncle.*—6.5-7.1 cm.

*Peduncle diameter.*—0.2 cm.

*Texture.*—Bifid hairs.

Inflorescence:

*Type.*—Compositae, solitary, decorative-type inflorescences borne terminally above foliage, ray florets arranges on a capitulum.

*Quantity of short days to flowering (response time).*—6.5 weeks.

*Natural season flowering.*—End of september.

*Quantity of inflorescences per plant.*—40-50 flowers, and many buds in various stages of development.

*Lastingness of individual blooms on the plant.*—About 5.5 weeks from first color.

*Fragrance.*—Slightly spicy.

Bud (when showing color):

*Color.*—Near RHS 183A.

*Length.*—0.8-1.3 cm.

*Width.*—0.9-1.1 cm.

*Shape.*—Oblate.

Immature inflorescence:

*Diameter.*—2.2-2.5 cm.

*Color of ray florets, upper surface.*—RHS 185A.

*Color of ray florets, lower surface.*—RHS 184B.

Mature inflorescence:

*Diameter.*—4.0-4.5 cm.

*Depth.*—1.0-1.5 cm.

*Total diameter of disc.*—0.3-0.4 cm.

*Receptacle color.*—RHS 145B.

*Receptacle height.*—0.3 cm.

*Receptacle diameter.*—0.3-0.4 cm.

Ray florets:

*Average quantity of florets.*—Between 140 and 170 in several whorls.

*Color of florets, upper surface (abaxial).*—RHS 187D.

*Color inner surface (adaxial).*—RHS 185B overlain with RHS 155B.

*Length.*—1.6-1.9 cm.

*Width/diameter.*—0.5-0.7 cm.

*Shape*.—Oblong to elliptical.
*Apex shape*.—Irregularly emarginate.
*Base shape*.—Attenuate.
*Margin*.—Entire.
*Texture, upper surface*.—Smooth and entire.
*Lower surface*.—Smooth and entire.

Disc florets:
*Average quantity of florets*.—10-15.
*Color of florets*.—RHS 1B, or slightly more greenish.
*Length*.—0.2-0.35 cm.
*Width*.—0.1 cm.
*Shape*.—Tubular, elongated.
*Apex shape*.—Acute, 5 pointed.

Phyllaries:
*Quantity*.—20-25.
*Color, upper surface*.—RHS 137A.
*Color, lower surface*.—RHS 137A.
*Length*.—0.6-0.7 cm.
*Width*.—0.2-0.3 cm.
*Shape*.—Lanceolate.
*Apex shape*.—Acute.
*Base*.—Fused.
*Margins*.—Entire, some with papery edges.
*Texture, upper surface*.—Glabrous.
*Texture, lower surface*.—Bifid hairs.

Reproductive organs:
*Pistil*.—One, found on both types of florets.
*Length*.—0.5-0.6 cm.
*Style color*.—RHS 1C.
*Style length*.—0.35-0.4 cm.
*Stigma color*.—RHS 7D.
*Stigma shape*.—Bi-lobed.
*Ovary color*.—RHS 145C.
*Ovary length*.—0.15 cm.
*Ovary width*.—0.1 cm.

Androecium:
*Stamens*.—4, found on only disc florets.
*Color of filaments*.—RHS 155C.
*Length filaments*.—0.15 cm.
*Anther color*.—RHS 6A.
*Anther length*.—0.1 cm.
*Anther shape*.—Oblong.
*Color of pollen*.—RHS 15C.
*Pollen amount*.—Moderate.
*Fertility/seed set*.—Has not been determined to date.
*Disease/pest resistance*.—Has not been determined to date.

What is claimed is:

1. A new and distinct variety of *Chrysanthemum* plant named 'CIFZ0044' substantially as illustrated and described herein.

* * * * *